United States Patent
Buerger et al.

[11] Patent Number: 5,985,299
[45] Date of Patent: Nov. 16, 1999

[54] PORE CLEANING PRODUCT

[75] Inventors: Douglas E. Buerger; Thomas J. Atkins, both of York, Pa.

[73] Assignee: Hercon Laboratories Corporation, Emigsville, Pa.

[21] Appl. No.: 09/063,546

[22] Filed: Apr. 20, 1998

[51] Int. Cl.$^6$ ..................................................... A01N 25/34
[52] U.S. Cl. ..................... 424/402; 424/78.03; 424/404
[58] Field of Search .................................. 424/78.03, 402, 424/404

[56] References Cited

U.S. PATENT DOCUMENTS

| | | | |
|---|---|---|---|
| 3,862,310 | 1/1975 | Quasius | 424/70 |
| 4,126,142 | 11/1978 | Saute | 132/7 |
| 4,421,602 | 12/1983 | Brunnmueller, et al. | 162/168.2 |
| 4,824,913 | 4/1989 | Murao, et al. | 525/344 |
| 5,026,522 | 6/1991 | Gueret, et al. | 424/401 |
| 5,430,110 | 7/1995 | Ahlers, et al. | 525/328.2 |
| 5,512,277 | 4/1996 | Uemura, et al. | 424/78.03 |
| 5,609,857 | 3/1997 | Chandran, et al. | 424/70.1 |
| 5,632,977 | 5/1997 | Chandran, et al. | 424/70.17 |

FOREIGN PATENT DOCUMENTS

| | | | |
|---|---|---|---|
| 0 262 577 | 4/1988 | European Pat. Off. | C08F 8/12 |
| 0 282 823 | 9/1988 | European Pat. Off. | A61K 7/48 |
| 0 514 760 B1 | 11/1992 | European Pat. Off. | A61K 7/48 |
| 0 826 364 A2 | 3/1998 | European Pat. Off. | A61K 7/48 |
| WO 97/32567 | 9/1997 | WIPO | A61K 7/48 |

*Primary Examiner*—S. Mark Clardy
*Assistant Examiner*—Kathryne E. Shelborne
*Attorney, Agent, or Firm*—Wolf, Greenfield & Sacks, P.C.

[57] ABSTRACT

Cosmetic products and methods of performing skin treatments are disclosed. The products and methods are especially suitable for removing keratotic plugs from the pores of skin. The cosmetic products are based on formulations including non-ionic, film-forming, solvent-activatable polymers as major active ingredients. Especially preferred formulations include N-vinyl formamide as in poly(N-vinyl formamide) as a major active ingredient. In some cases, the formulations are coated onto a backing material to form a patch in order to increase the utility and ease of use of the products. The products are used to remove keratotic plugs by applying the product to the skin, allowing the product to dry, and peeling the product from the skin. Also disclosed is a method for producing the preferred articles provided by the invention.

61 Claims, 4 Drawing Sheets

PORE CLEANING PRODUCT

FIELD OF THE INVENTION

The invention relates generally to cosmetic formulations and products for skin treatment, and more specifically to formulations and methods for removing keratotic plugs from the pores of the skin involving film-forming polymers.

BACKGROUND OF THE INVENTION

Keratotic plugs are formed in pores of living human skin from dead epidermal cells that have become keratinized together with sebaceous material and dirt. The presence of keratotic plugs in the pores of the skin leads to an unsightly increase in the visibility of the pores and can also lead to dermatological problems such as skin infection. Thus, for both cosmetic and heath reasons, it is advantageous to remove keratotic plugs from the pores of the skin.

Keratotic plugs, however, can be difficult to effectively remove from the skin in a gentle fashion. Prior art skin cleansers and detergents are limited in their ability to remove keratotic plugs quickly, gently and effectively. Mechanical means of removing keratotic plugs, for example by squeezing, pressing, or creating a suction on the skin, can cause undo pain and skin damage, and are generally slow and tedious to perform since only a small number of plugs can be removed at a time.

Water-activated film-forming packs and masks have previously been used to cleanse and strip the skin. Such formulations generally utilize a film-forming cosmetic formulation, which is applied to the skin, allowed to dry, and peeled from the skin after drying. The formulations can either be applied to the face directly, or can be pre-coated onto a support backing. U.S. Pat. No. 4,126,142 discloses a skin treating technique where a material which can be a film of sodium polystyrene sulfonate cosmetic solution is applied to the skin, allowed to dry, and subsequently peeled off, removing scurf skin and sebaceous soils. U.S. Pat. No. 5,512,277 teaches a keratotic plug removal method using a film forming composition comprising an ionic polymer having a salt forming group which is peeled from the skin. This patent further teaches that non-ionic polymer formulations are not sufficiently effective for desired use in effectively removing keratotic plugs by the same method.

Cosmetic formulations comprising non-ionic polymers can be advantageous from the standpoint of gentleness to the skin and ease of formulation and processing. Accordingly, it is an object of the present invention to provide effective cosmetic products and methods utilizing non-ionic, non-salt-forming polymer-based formulations for removal of keratotic plugs from the skin.

SUMMARY OF THE INVENTION

Novel cosmetic products, methods, and articles are described herein for performing skin treatments, especially for removing keratotic plugs. In one aspect, the invention provides a cosmetic product for the treatment of skin comprising a non-ionic, non-salt-forming polymer composition. The product is formulated to facilitate removal of more than 10% of keratotic plugs from an area of skin by peeling a substantially dry layer of the product from that area of skin.

In another embodiment, the invention involves a cosmetic product for performing a skin treatment. The product comprises a water-activatable, film-forming polymeric composition being selected from the group consisting of copolymers of N-vinyl formamide with at least one vinyl monomer and poly(N-vinyl formamide) homopolymer, with N-vinyl formamide of said polymeric composition as a major, active component. The polymeric composition is formulated to have predetermined properties for allowing desired adhesion of a layer of the composition to the skin of an individual and to any keratotic plugs contained therein. The product also facilitates removal of keratotic plugs, via removal of the layer from the skin, without causing damage to the skin.

In yet another embodiment, the invention provides a cosmetic product for treating the skin that includes a combination of components. The product includes a non-ionic, non-salt-forming polymer composition having poly(N-vinyl formamide) or N-vinyl formamide of a copolymer as a major active ingredient. The product further includes at least one softening agent, at least one opacifier, at least one preservative, and may include a variety of other suitable components known in the art of cosmetic formulations. The product is formulated to remove more than 10% of keratotic plugs present on an area of skin by peeling a substantially dry layer of the product from that area of skin.

In another aspect, the invention provides an article for application to skin. The article comprises a backing material with a composition comprising a non-ionic, non-salt-forming polymer being coated onto one side of the backing material forming a patch. The patch, coated on one side with the composition, is able to remove more than 10% of keratotic plugs present on an area of skin by peeling the patch from that area of skin.

In another embodiment, the invention involves an article for application to skin comprising a composition forming a layer on one side of a backing material, thus forming a patch. The composition forming the layer preferably comprises poly(N-vinyl formamide).

The invention also provides methods for treating skin. In one aspect, the invention involves a method for removing keratotic plugs from skin. The method involves providing, in contact with and overlying skin having keratotic plugs, a composition comprising poly(N-vinyl formamide) or a copolymer of N-vinyl formamide with at least one vinyl monomer. The composition is allowed to substantially dry, and is subsequently peeled away from the skin.

In another embodiment, the invention provides a method for removing keratotic plugs from the skin with a patch that is coated on at least one side with a composition comprising poly(N-vinyl formamide) or a copolymer of N-vinyl formamide with at least one vinyl monomer. The method involves applying the composition carried by the patch to skin, so that it is in contact with and overlies the skin, and, subsequently, removing the patch from the skin.

In another embodiment, the invention entails a method for removing more than 10% of keratotic plugs from an area of skin. The method involves providing a patch that is coated on at least one side with a composition including at least one non-ionic, non-salt-forming polymer. The method further involves applying the composition carried by the patch so that it overlies and is in contact with the skin, and, subsequently, removing the patch from the skin.

In yet another aspect, the invention involves a method of adhering a patch to skin. The method entails providing a patch that is coated on at least one side with a composition including poly(N-vinyl formamide) or a copolymer of N-vinyl formamide with at least one vinyl monomer. The method subsequently involves applying the patch to moistened skin and allowing the patch to substantially dry. In another embodiment, the method involves providing a patch that is coated on at least one side with a composition including poly(N-vinyl formamide) or a copolymer of N-vinyl formamide with at least one vinyl monomer, moistening at least one surface of the patch, applying the moistened patch to skin, and allowing the patch to substantially dry.

The invention also provides a process for manufacturing a patch that is coated on at least one surface with a composition comprising a solvent-dispersable polymer or copolymer of this invention. The process involves coating a release liner with the composition dispersed in a solvent. After coating, the solvent is partially removed from the composition by drying, and a porous backing material is then applied to the partially dry composition. The composition is then allowed to partially penetrate into the porous backing material, and, in a separate drying step, additional solvent is subsequently removed from the resulting article.

BRIEF DESCRIPTION OF THE DRAWINGS

Other advantages, novel features, and objects of the invention will become apparent from the following drawings when considered in conjunction with the accompanying specification, which drawings are schematic and which are not intended to be drawn to scale. In the figures, each identical or nearly identical component that is illustrated in various figures is represented by a single numeral. For purposes of clarity, not every component is labeled in every figure. In the drawings.

DETAILED DESCRIPTION

The present invention provides cosmetic products for effectively removing keratotic plugs from an area of skin which is treated with the products. The products and methods described herein are effective in removing a substantial fraction of the keratotic plugs initially present in the untreated skin. Preferred embodiments of the invention are able to remove in excess of 10% of the keratotic plugs initially present in the untreated skin. More preferred embodiments are able to remove at least 20%, and most preferred embodiments are able to remove at least 35% of the keratotic plugs initially present in the untreated skin. These removal amounts can be obtained by a single application of a cosmetic product of this invention with additional amounts removed, in some cases, by multiple applications.

The present invention provides novel cosmetic compositions containing non-ionic polymeric components. Non-ionic as used herein refers to uncharged molecular species that are free of ionizable, salt-forming groups. Typical salt-forming groups are those that can form a salt in the presence of an acid or a base and include anionic, cationic, and amphoteric groups. The preferred non-ionic polymers for use in the invention are solvent-activatable, film-forming polymers. Especially preferred are water-activatable, film-forming polymers that are also water-activated adhesives. A water-activatable, film forming polymer as used herein refers to a polymeric composition that is soluble or dispersable in water and that is able to form a continuous layer on a surface when a solution or dispersion of the composition is applied to the surface and the water is partially or completely removed by evaporation. A water-activatable adhesive as used herein refers to a water-activated, film-forming polymeric composition where the layer formed on a surface as described above forms an adhesive bond with the surface that requires mechanical force to disrupt. Polymers suitable for use in the present invention are preferably water soluble; however, the polymer need not be water soluble to be suitable for achieving the effects of the invention. Alternatively, the polymers may simply be dispersable in ater or other solvent to form an emulsion or dispersion.

The cosmetic compositions provided by the present invention each include a non-ionic, solvent- or water-activatable, film-forming polymer as a major active component. By major active component it is meant that the particular component is an indispensable component for obtaining the desirable pre-determined properties (discussed below) of a polymeric layer formed from the composition upon contact with a surface, such as skin, and partial or complete removal of the solvent. Non-ionic polymers that are useful in the invention include poly(vinyl alcohol), poly(vinyl pyrrolidone), polyacrylamide, poly(ethylene oxide), dimethicone copolyol, poly(hydroxyethyl methacrylate), and others. Especially preferred in view of its excellent film-forming and adhesive properties as well as its mildness to the skin and effectiveness at removing keratotic plugs is poly(N-vinyl formamide). Poly(N-vinyl formamide) is a homopolymer of N-vinyl formamide that can be formed by standard free radical polymerization techniques known in the art. Exemplary methods of synthesizing poly(N-vinyl formamide) are disclosed in U.S. Pat. No. 4,421,602 and U.S. Pat. No. 4,824,913 incorporated herein by reference. Polymeric compositions for use in the invention can also comprise mixtures of the above mentioned polymers.

The polymer may be a homopolymer of N-vinyl formamide or may be a copolymer prepared from N-vinyl formamide and at least one vinyl monomer(s). Preferably, the copolymer will comprise at least about 80 weight percent of N-vinyl formamide, with the balance of the vinyl monomer (s). The term "vinyl monomer," as used herein, refers to vinyl monomers which are copolymerizable with the N-vinyl formamide. Suitable vinyl monomers include, (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl substituted acrylamides and methacrylamides of the formula $CH_2$=CR—$CONR_1R_2$ where R is H or $CH_3$; $R_1$ is H or $C_1C_{12}$ and $R_2$ is $C_1$–$C_{18}$, (f) diesters of fumaric, itaconic and malcic acids, (g) vinyl ethers such as methyl vinyl ether, isobutyl vinyl ether and the like, (h) hydroxy functional acrylates and methacrylates such as hydroxyethyl acrylate, hydroxypropyl acrylate, hydroxyethyl methacrylate, hydroxypropyl methacrylate and the like, (i) amine monomers such as butylaminoethyl methacrylate, dimethylaminoethyl methacrylate, diethylaminoethyl methacrylate and the quarternized derivatives thereof such as trimethylmethacrylatoethyl ammonium chloride and trimethylmethacrylatoethyl ammonium sulfate, (j) acrylamide and non-alkyl substituted acrylamides such as diacetone acrylamide, and (k) cyclic amides such as vinyl pyrrolidone. Preferably, the vinyl comonomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate and oligoethylene glycol monomethacrylate.

Preferred cosmetic products according to the present invention include compositions that are formulated to have predetermined properties for allowing desired adhesion of a layer of the composition to the skin, and to the keratotic plugs that are present in the skin. These predetermined properties depend upon the particular make up of the composition as applied to the skin. Desirable predetermined properties from the standpoint of effectively removing keratotic plugs include the following. Preferred formulations should be capable of forming a cohesive layer upon the skin after application to the skin and subsequent drying. The layer should adhere strongly to keratotic plugs so that they are removed, along with the layer, due to their adherence. The layer should possess sufficient strength and flexibility to be able to be removed from the skin in substantially one piece by peeling. The most preferred formulations can be peeled from the face without causing damage, as evidenced by undo pain or injury, to the skin, yet are able to pull out a substantial fraction of the keratotic plugs from the pores of the skin as previously discussed.

Formulations according to the present invention preferably include at least a film-forming non-ionic polymer or copolymer and a suitable solvent, preferably water. As previously discussed, the most preferred embodiments include poly(N-vinyl formamide) as a major active ingredient. Preferably, the solvent comprises 10–90% wt of the total formulation, more preferably 30–70% wt, and most preferably 40–60% wt. Various other ingredients common to the cosmetic industry can be added to the formulation as desired. Ingredients such as skin softeners, opacifiers, stabilizers, preservatives, diluent polymers, and the like can be included to provide desirable properties to the overall composition. Preferably, the active film forming polymer, for example poly(N-vinyl formamide) or copolymer of N-vinyl formamide, comprises 50–100% wt of the composition on a dry (solvent-free) basis. Also, preferably the active film-forming polymer or copolymer has a molecular weight (weight average) in the range from 10,000 to 1,500,000, more preferably from 50,000 to 500,000, and most preferably from 100,000 to 200,000. Preferably N-vinyl formamide comprises 50–1 00% wt of the composition on a dry (solvent-free) basis.

In some case the N-vinyl formamide homopolymer or copolymer can be formed into films useful in this invention without use of solvents as in calendering or extrusion methods.

Preferable skin softening components prevent irritation to the skin, improve skin feel, and can increase the strength and flexibility of the peelable layer. A partial and non-limiting list of suitable softeners includes oils such as vegetable, mineral, animal, silicone, or glycerol derivatives, or other suitable materials such as glycerin, propylene glycol, hexylene glycol, dipropylene glycol, propylene glycol dicaprylate, diethylene glycol, sorbitan monooleate, polyethylene glycol (PEG), ethylene glycol, triethylene glycol, polypropylene glycol (PPG), butylene glycols, sugaralcohols, ethylene oxides, mono- and polysaccharides, and surfactants. Preferred softening agents include glycerin, propylene glycol, hexylene glycol, dipropylene glycol, propylene glycol dicaprylate, diethylene glycol, sorbitan monooleate, and polyethylene glycol (PEG). One or more of the softening components can be used. The softening agent or components preferably comprises from 0–20% wt of the overall composition on a dry basis, and more preferably 2–12% wt.

Some preferred embodiments of the invention further include an opacifying pigment in the overall composition. A wide variety of one or more suitable pigments known in the art can be employed including both inorganic and organic pigments. Examples of suitable inorganic pigments include titanium dioxide, aluminum oxide, silicone dioxide, zinc oxide, silica, alumina, boron nitride, hydroxyapatite, ceramics, zirconium oxide, calcium silicate, calcium carbonate, barium sulfate, talc, mica, sericite, montmorillonite, saponite, kaolin, hectorite, iron oxide, etc. Suitable organic opacifiers include cellulose acetate butyrate, poly(methyl methacrylate), poly(vinyl chloride), ethyl cellulose, silk powders, rake pigments, azo dyes, and a wide variety of other polymer resins. Preferred opacifiers for the present invention include titanium dioxide, aluminum oxide, silicone dioxide, cellulose acetate butyrate, poly(methyl methacrylate), poly(vinyl chloride), and ethyl cellulose. The opacifier preferably comprises from 0–10% wt of the overall composition on a dry basis, and more preferably 1–8% wt.

In some embodiments, the formulation includes one or more preservatives to stabilize the composition and/or prevent the growth of bacteria, and/or molds. A variety of suitable materials known in the art of cosmetic formulation may be used in this context, for example, methyl paraben, benzalkonium chloride, benzlylparaben, calcium acetate, captan, chloroacetamide, dichlorobenzyl alcohol, DMDM hydantoin, imidazolidinyl urea, isopropylparaben, quatemium-15, sodium benzoate, and others. A preferred preservative for use in the present invention is methyl paraben. The preservative preferably comprises from 0–2% wt of the overall composition on a dry basis, more preferably 0–1% wt, and most preferably around 0.5% wt.

In additional embodiments, fillers or diluent polymers can be added to the overall composition, thus forming a polymer mixture, to enhance desirable properties, such as the film-forming properties of the polymer mixture, and/or the mechanical properties of the resulting film layer. Suitable polymers in this context include dimethicone copolyol, poly(ethylene oxide), poly(vinyl acetate), poly(vinyl pyrrolidone), vinyl pyrrolidone-vinyl acetate copolymer and similar copolymers, maleic anhydride-methyl vinyl ether copolymer and similar copolymers, polyvinyl alcohol and its copolymers, polyacrylic acid, and natural water soluble polymers, and the like, and mixtures thereof Especially preferred are dimethicone copolyol, poly(ethylene oxide), poly(vinyl acetate), poly(vinyl pyrrolidone), vinyl pyrrolidone-vinyl acetate copolymer, and mixtures thereof. The diluent polymer preferably comprises from 0–30% wt of the overall composition on a dry basis.

Other components can also be included in the overall composition to impart other desirable properties to the formulation, for example, vitamins, fatty acid esters, ultra-violet light absorbers, peripheral vasodilators such as methyl salicylate and nicotinic acid and its esters, herbal additives, powdered milk, proteolytic enzymes, vegetable powders, fruit extracts, egg solids or oil, starches, clays, amino acids, proteins, astringents, drugs, and the like. The compositions according to the invention, which are effective for removing keratotic plugs, can be mixed and manufactured according to conventional processes for producing cosmetic formulations.

Figure 1:
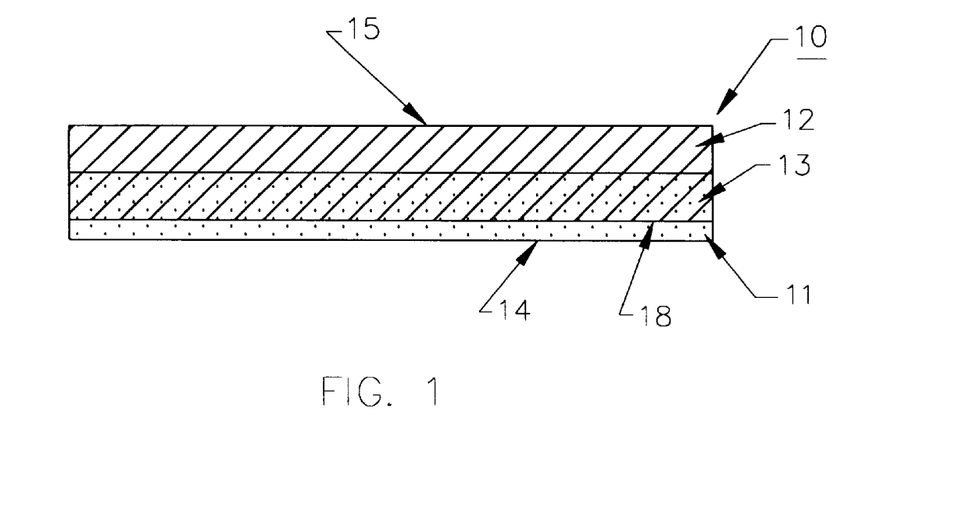
FIG. 1 illustrates schematically a cross-sectional view of a keratotic plug removing article according to the invention.

Referring now to the figures, FIG. 1 shows a preferred embodiment of the invention where the formulations previously described are utilized for keratotic plug removal in combination with a support backing 12, hereinafter also referred to as a backing material. The backing material may be any suitable porous or non-porous support for example cotton cloth, rayon cloth, nylon cloth, woven or non-woven plastic or polymer sheets, meshes, mats, plastic films, and the like. The backing material may be applied to the keratotic plug removing composition after it has been applied to the skin but before significant drying has occurred, or preferably, the composition is applied to the backing material and subsequently applied to the skin for the removal of keratotic plugs. It can be appreciated that use of the composition in combination with a backing material offers several advantages. First, the backing material provides support to the polymeric layer when peeling away from the skin. Second, the backing material increases the ease and convenience of application of the composition to the skin and its removal from the skin. Suitable backing materials must be sufficiently adherent to the composition upon drying so that upon peeling, the composition is preferentially removed from the skin as opposed to being removed from the backing material. Preferably, the backing material is sufficiently flexible to conform to the natural curvature of the skin surface to which it is applied. The backing material is also, preferably, sufficiently gas permeable to allow the composition to dry sufficiently in a reasonable period of time. Accordingly, relatively thin porous backing materials are preferred. The porosity of the preferred backing materials also allows the composition to penetrate into the interstices of the material thus increasing the adhesion strength of the composition to the backing material. It is generally undesirable, however, for the composition to be completely absorbed by the backing material during use. For this reason, hydrophobic backing materials are preferred over hydrophillic. Especially preferred are non-woven fibrous mats, such as spun-bonded or point-bonded polyester or polyolefin fiber or the like. The preferred thickness of the porous backing material is from 0.05 to 2 mm, more preferably from 0.1 to 0.5 mm, and most preferably from 0.2 to 0.4 mm.

FIG. 1 additionally shows a preferred arrangement of a keratotic plug removing article 10 according to the present invention. In this embodiment, the article has been prepared by coating one side 18 of a backing material 12 with a keratotic plug-removing composition previously described and subsequently allowing the composition to dry. The resulting article, hereinafter also referred to as a "coated patch" or a "patch," is a multi-layered structure comprising a backing material 12, a layer of substantially dry keratotic plug-removing composition 11, and a region 13 of the backing material 12 that contains dried keratotic plug removing composition that has penetrated into the porous structure. "Substantially dry" as used herein refers to a composition that is dry to the touch but that may contain some residual solvent or water, typically around 10–15% wt of the total composition. The article 10 provides a convenient and easily packagable keratotic plug removing device. The article is conveniently used, as described in greater detail below, by applying moisture to the coated patch immediately prior to use, or applying the coated patch to moistened skin, thus activating the water-activatable film-forming adhesive composition.

Figure 2:
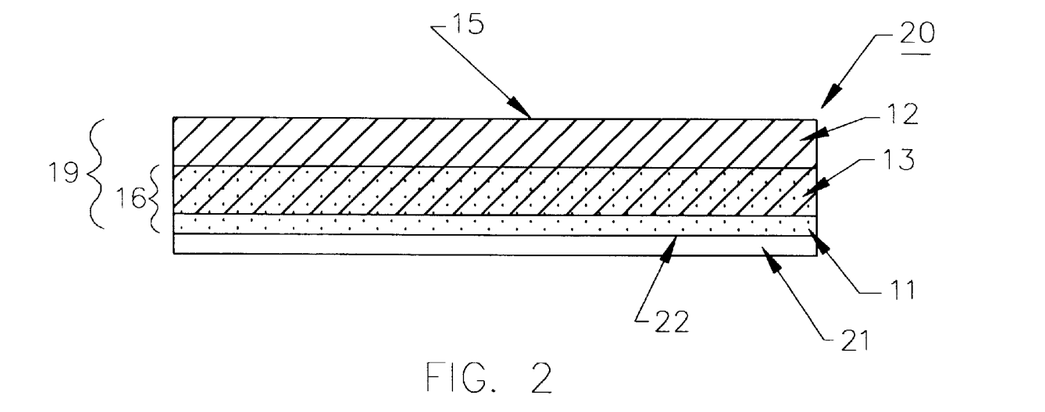
FIG. 2 illustrates schematically a cross-sectional view of a keratotic plug removing article including a release liner.

FIG. 2 shows an article 20 similar to that of FIG. 1. The article 20 also has a release liner 21 releasably adhered to the keratotic plug-removing composition layer 11. It should be noted that the figures are not drawn to scale and that the thickness of the release liner 21 may, in some embodiments, be comparable to or exceed that of the backing material 12. The release liner serves to protect the composition from damage prior to use. Preferred release liners are thin, non porous polymer sheets, such as polyester films readily available for use as release liners. Preferably, the composition should be weakly attached to the liner so that the liner can be easily removed by the user without damaging the keratotic plug-removing composition layer 11. Accordingly, in certain embodiments, preferred release liners are silicone-coated. In some embodiments for producing (described in more detail below) keratotic plug-removing article 20, the keratotic plug-removing composition is advantageously cast onto one side 22 of the liner 21 and subsequently covered with a backing material 12 before the composition has thoroughly dried so that the composition can partially penetrate the backing material 12 forming a region 13 of the backing material 12 that contains keratotic plug-removing composition. The significance of region thicknesses 16 and 19 are discussed below.

Figure 3:
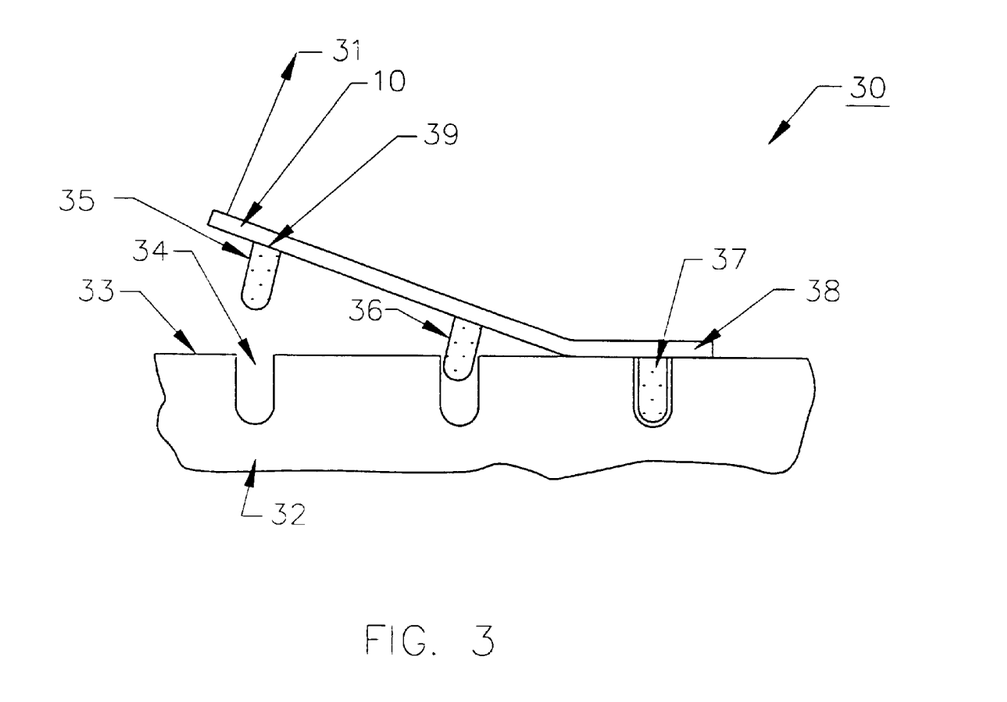
FIG. 3 illustrates schematically a method step according to the present invention for removing keratotic plugs from skin.

FIG. 3 shows the keratotic plug removal step 30 of a preferred method of skin treatment according to the invention. In the method, the skin 32 is first moistened. The user then applies a keratotic plug-removing patch 10 to the moistened skin so that the keratotic plug-removing composition layer surface (see FIG. 1, element 14) is overlying and in contact with the moist skin. The coated patch, once it is applied, loses its stiffness because the composition rehydrates in contact with the moistened skin. Under these conditions, the patch resumes its supple and flexible nature and becomes deformable, enabling it to mold to the irregularities of the skin surface. The patch adheres to the skin, initially in the form of moisture contact, and then, after drying, in the form of a dry adhesive. Within about 10–30 minutes after application, the keratotic plug-removing composition substantially dries in air to a substantially dry state. At this point, as illustrated in FIG. 3, a peeling force 31 is applied to the patch 10 to separate the keratotic plug-removing composition from the skin surface 33. Since the bond 39 between the composition and the keratotic plugs 35, 36, 37 is stronger than the force required to remove the keratotic plugs 35, 36, 37 from the pores (e.g. 34), a substantial fraction of the keratotic plugs will be pulled from the pores upon peeling the patch 10 from the surface 38 of the skin 32. Alternatively, the method outlined above can be modified so that the coated patch is moistened prior to application to the skin instead of pre-moistening the skin. In some cases, a surface layer of the epidermis may be removed along with the patch, and in other cases, substantially only the keratotic plugs are removed.

For embodiments where a keratotic plug-removing composition is used directly to perform a skin treatment without having been pre-coated onto a backing material and substantially dried, methods for removing keratotic plugs from the skin are somewhat modified from those outlined above. Preferably, the keratotic plug-removing composition is supplied in a hydrated state to the user. The user would then apply the composition directly to the skin to be treated thus forming a layer. After allowing sufficient time for the layer to become substantially dry, the user would subsequently peel (as shown in FIG. 3) away the dried layer 10 to remove a substantial fraction of the keratotic plugs 35, 36, and 37. Advantageously, a backing material, according to the invention, could be applied to the layer, after it has been applied to the skin but before it has become substantially dry, in order to facilitate easier peeling. Alternatively, the composition could be applied to one side of a backing material, thus forming a patch, immediately prior to applying the composition on the patch to the skin. Less preferably, the keratotic plug-removing composition (not coated onto a backing material) could be supplied in a substantially dry form which would be reconstituted with water by the user prior to use.

It should also be appreciated that the methods and articles of the invention also provide a novel means of removably attaching a polymeric layer or a patch containing a polymeric layer to skin using poly(N-vinyl formamide) as a water-activatable, film-forming adhesive. Such attached layers and patches can have many potential uses beyond that of removing keratotic plugs, for example for wound dressing, incision closing, skin retraction, bandaging, drug delivery, skin softening, cosmetic delivery and others.

Figure 4:
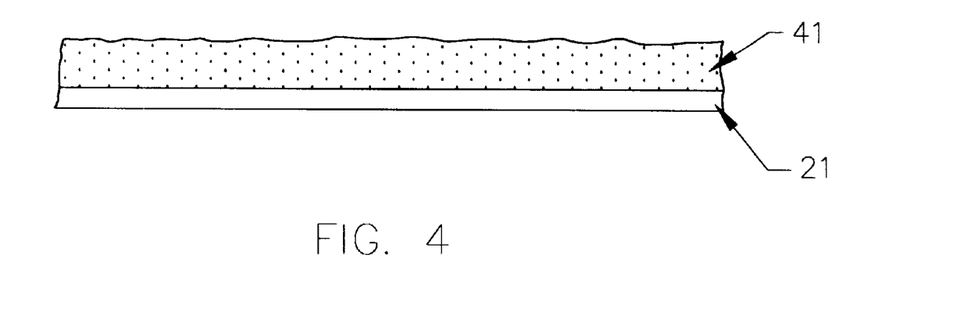
FIG. 4 illustrates schematically a coating step in a process for producing skin treating articles according to the invention.
Figure 5:
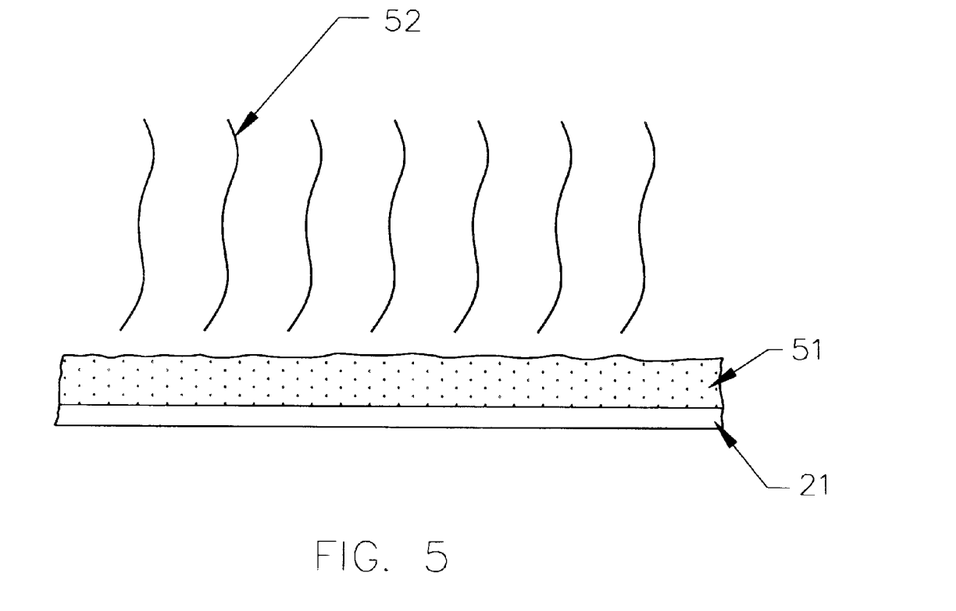
FIG. 5 illustrates schematically a first drying step for producing skin treating articles according to the invention.
Figure 6:
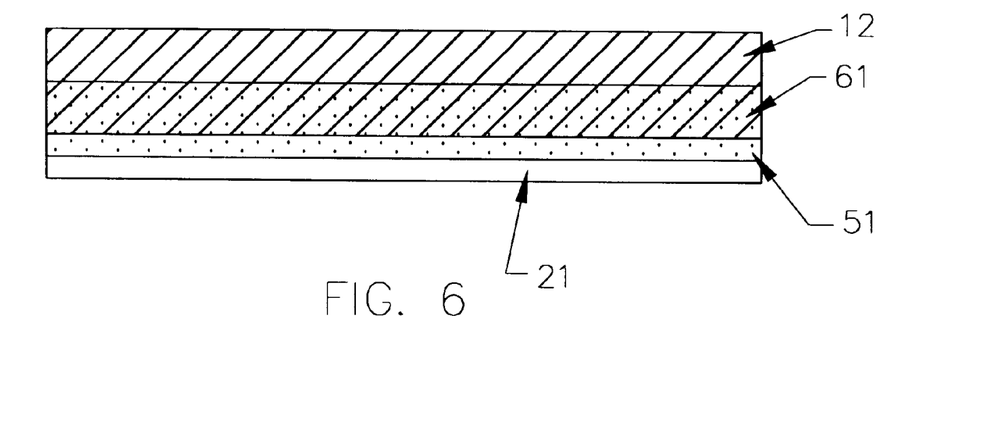
FIG. 6 illustrates schematically a backing material application step for producing skin treating articles according to the invention.
Figure 7:
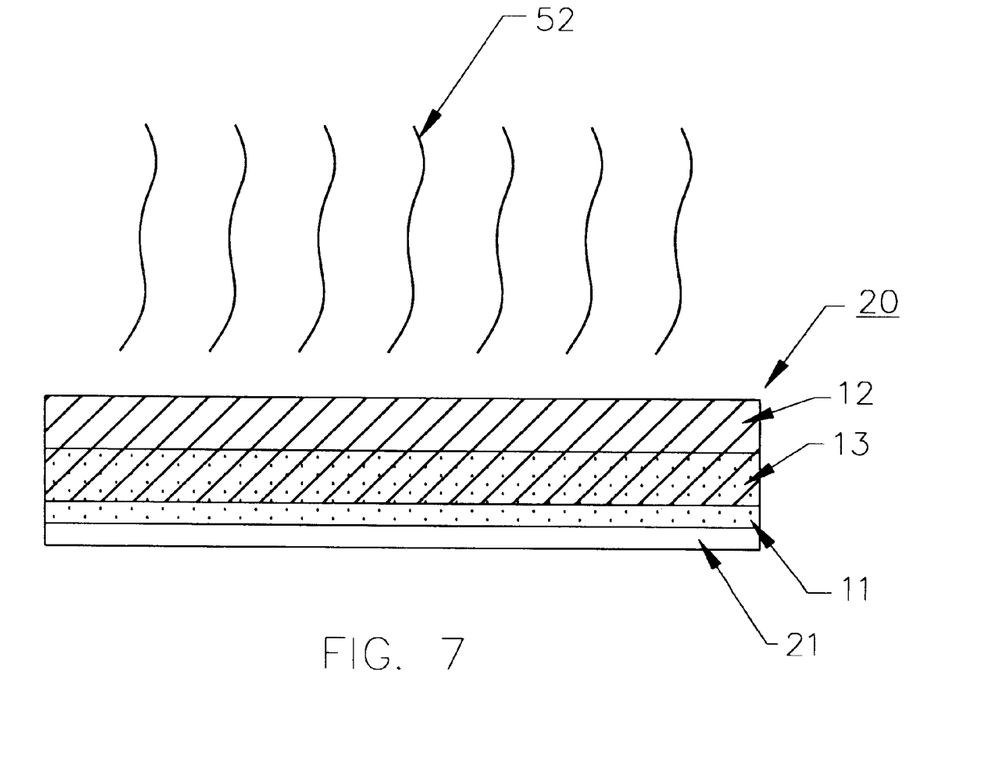
FIG. 7 illustrates schematically a second drying step for producing skin treating articles according to the invention.

The invention also provides a process for producing the keratotic plug-removing articles shown in FIG. 2. The process is outlined schematically in FIGS. 4–7 and may be performed in either a batch or continuous mode. In step 1 of the, process shown in FIG. 4, a keratotic plug-removing composition 41 formulated as described previously and dispersed or dissolved in sufficient solvent, preferably water, so that the composition is flowable in a liquid or gel-like state, is coated onto a release liner 21 by standard methods. In step 2, shown in FIG. 5, the composition on the release liner 21 is partially dried to remove part of the solvent by evaporation 52, thus forming a semi-dry composition layer 51 on the liner 21. This step can advantageously be performed utilizing a warm air oven at about 50–70 degrees C for 2.5–15 minutes. Preferably, at the end of step 2, the composition 51 has a solvent or water content between about 25–35% wt. In step 3, shown in FIG. 6, the semi-dried composition 51 is covered with a sheet of porous backing material 12, and the composition 51 is allowed to partially penetrate the sheet forming a semi-dry-composition-containing layer 61 within the sheet. In the final step, shown in FIG. 7, the article from FIG. 6 is subjected to an additional drying step, either as previously described or at room temperature, to evaporate additional solvent 52 until the composition 11 is substantially dry (about 0–15% wt residual solvent). This yields an article 20 comprising a backing material 12, a release liner 21, a keratotic plug removing composition layer 11, and a region 13 of the backing material 12 containing keratotic plug removing composition. Finally, the article can be cut into smaller articles of desired size for use and packaged according to standard methods. It should be appreciated that the conditions above are typical values but that the precise conditions required to obtain the best results from the processing steps outlined above will vary depending on factors such as the make up of the composition, the amount of the composition coated per unit area of the liner, and the properties of the backing material.

Use of this process allows the initial coating step to proceed more efficiently because of the relatively lower viscosity of the more hydrated composition 41, but also enables the degree of penetration of the composition to be more precisely and easily controlled by contacting the backing material 12 in step 3 with a more viscous, less hydrated composition 51, which penetrates into the pores of the material more slowly. Utilizing this method, keratotic plug-removing articles can be produced that have a desirable degree of composition penetration into the backing material sheet. Referring now to FIG. 2, preferred articles have a penetration depth 16 that is between 30 and 70% the cross-sectional thickness 19 of the backing material. The final thickness of the layer of keratotic plug-removing composition on the patch after drying, and the degree of penetration into the backing material, is also affected by the amount of composition coated onto the releasable liner in step 1. Preferably, the liner is coated with about 1 to 6 ounces of composition, on a dry weight basis, per square yard of liner, more preferably about 4 ounces, thus, yielding a final article with about 1 to 6 ounces of composition, on a dry weight basis, per square yard of coated patch, more preferably about 4 ounces.

The function and advantage of these and other embodiments of the present invention will be more fully understood from the examples below. The following examples are intended to illustrate the benefits of the present invention, but do not exemplify the full scope of the invention.

EXAMPLE 1

A composition containing the ingredients listed in Table 1 is coated onto a silicon-coated polyester release liner at a wetcoat thickness of 0.50 millimeter. The wet film is then covered with a porous non-woven polyester fabric (thickness of 0.27 millimeter) and dried for 20 minutes in a warm air oven at about 68 degrees C.

The dried material is then cut into 18 millimeter by 72 millimeter patches coated with the dried composition and covered by a release liner. The release liner is first removed, and then the coated patch is then applied to wet skin across the bridge of the nose, so that the composition on the patch is overlying and in contact with the skin. The patch is then allowed to dry for about 15 minutes and subsequently peeled from the nose. The removed patch displays keratotic plugs, dirt, and other material from the pores of the skin visibly adhered to the surface of the patch. The procedure removes a substantial fraction of the keratotic plugs initially present in the pores of the skin.

TABLE 1

| Ingredient | Amount (% wt based on total formulation) | Amount (% wt dry basis) |
|---|---|---|
| Poly (N-vinyl formamide), [National Starch Resin 78-6986, National Starch and Chemical Co., Bridgewater, NJ] | 40.3 | 89.5 |
| Glycerin [Penta Mfg. Co., Livingston, NJ] | 0.9 | 2.0 |
| Titanium Dioxide [Whittaker, Clark & Daniels, Inc. South Plainsfield, NJ] | 3.6 | 8.0 |
| Methyl Paraben [Penta Mfg. Co., Livingston, NJ] | 0.2 | 0.5 |
| Water | 55.0 | — |

EXAMPLE 2

A composition containing the ingredients listed in Table 2 is prepared and coated in the same fashion as for Example 1. In all examples unless otherwise noted the ingredients which are the same as in Example 1 are same products as Example 1 obtained from the sources of these products set forth in Example 1. The coated patch is tested on the wetted bridge of the nose in a similar manner as in Example 1. Upon removal, the patch strips keratotic plugs and other materials from the pores of the skin. The materials removed from the pores are difficult to visualize on the surface of the patch since the formulation contains no pigment.

TABLE 2

| Ingredient | Amount (% wt based on total formulation) | Amount (% wt dry basis) |
|---|---|---|
| Poly (N-vinyl formamide) | 50.0 | 100.0 |
| Water | 50.0 | — |

EXAMPLE 3

A composition containing the ingredients listed in Table 3 is prepared and coated onto a silicone-coated polyester release liner at a wetcoat thickness of 0.35 millimeter. The wet film is partially dried (to a water content of 25% wt) in a warm air oven at 68 degrees C., then covered with a porous, non-woven polyester fabric (thickness of 0.27 millimeter), and further dried in a warm air oven at 68 degrees C. until substantially dry (having 14% wt residual water content).

The dried material is then cut and tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 3

| Ingredient | Amount (% wt based on total formulation) | Amount (% wt dry basis) |
|---|---|---|
| Poly (N-vinyl formamide) | 39.3 | 85.5 |
| Glycerin | 2.8 | 6.0 |
| Titanium Dioxide | 3.7 | 8.0 |
| Methyl Paraben | 0.2 | 0.5 |
| Water | 54.0 | — |

EXAMPLE 4

A composition containing the ingredients listed in Table 4 is prepared and coated in a manner similar to Example 3. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 4

| Ingredient | Amount (% wt based on total formulation) | Amount (% wt dry basis) |
|---|---|---|
| Poly (N-vinyl formamide) | 38.4 | 83.5 |
| Glycerin | 3.7 | 8.0 |
| Titanium Dioxide | 3.7 | 8.0 |
| Methyl Paraben | 0.2 | 0.5 |
| Water | 54.0 | — |

EXAMPLE 5

A composition containing the ingredients listed in Table 5 is prepared and coated in a manner similar to Example 3. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 5

| Ingredient | Amount (% wt based on total formulation) | Amount (% wt dry basis) |
|---|---|---|
| Poly (N-vinyl formamide) | 36.6 | 79.5 |
| Glycerin | 5.5 | 12.0 |
| Titanium Dioxide | 3.7 | 8.0 |
| Methyl Paraben | 0.2 | 0.5 |
| Water | 54.0 | — |

EXAMPLE 6

A composition containing the ingredients listed in Table 6 is prepared and coated in a manner similar to Example 3. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 6

| Ingredient | Amount (% wt based on total formulation) | Amount (% wt dry basis) |
|---|---|---|
| Poly (N-vinyl formamide) | 41.2 | 89.5 |
| Glycerin | 2.8 | 6.0 |
| Titanium Dioxide | 1.8 | 4.0 |
| Methyl Paraben | 0.2 | 0.5 |
| Water | 54.0 | — |

EXAMPLE 7

A composition containing the ingredients listed in Table 7 is prepared and coated in a manner similar to Example 3. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 7

| Ingredient | Amount (% wt based on total formulation) | Amount (% wt dry basis) |
|---|---|---|
| Poly (N-vinyl formamide) | 42.1 | 91.5 |
| Glycerin | 2.8 | 6.0 |

TABLE 7-continued

| Ingredient | Amount (% wt based on total formulation) | Amount (% wt dry basis) |
| --- | --- | --- |
| Titanium Dioxide | 0.9 | 2.0 |
| Methyl Paraben | 0.2 | 0.5 |
| Water | 54.0 | — |

EXAMPLE 8

A composition containing the ingredients listed in Table 8 is prepared and coated in a manner similar to Example 3. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 8

| Ingredient | Amount (% wt based on total formulation) | Amount (% wt dry basis) |
| --- | --- | --- |
| Poly (N-vinyl formamide) | 42.6 | 92.5 |
| Glycerin | 2.8 | 6.0 |
| Titanium Dioxide | 0.5 | 1.0 |
| Methyl Paraben | 0.2 | 0.5 |
| Water | 54.0 | — |

EXAMPLE 9

A composition containing the ingredients listed in Table 9 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 9

| Ingredient | Amount (% wt based on total formulation) | Amount (% wt dry basis) |
| --- | --- | --- |
| Poly (N-vinyl formamide) | 41.2 | 89.5 |
| Glycerin | 2.8 | 6.0 |
| Aluminum Oxide [ICN Biomedicals, Eschwege, Germany] | 1.8 | 4.0 |
| Methyl Paraben | 0.2 | 0.5 |
| Water | 54.0 | — |

EXAMPLE 10

A composition containing the ingredients listed in Table 10 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 10

| Ingredient | Amount (% wt based on total formulation) | Amount (% wt dry basis) |
| --- | --- | --- |
| Poly (N-vinyl formamide) | 41.2 | 89.5 |
| Glycerin | 2.8 | 6.0 |
| Silicon Dioxide [Cabot Corp. Tuscola, IL] | 1.8 | 4.0 |
| Methyl Paraben | 0.2 | 0.5 |
| Water | 54.0 | — |

EXAMPLE 11

A composition containing the ingredients listed in Table 11 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 11

| Ingredient | Amount (% wt based on total formulation) | Amount (% wt dry basis) |
| --- | --- | --- |
| Poly (N-vinyl formamide) | 41.2 | 89.5 |
| Glycerin | 2.8 | 6.0 |
| Cellulose Acetate Butyrate, [FMC, Corp., Newark, DE] | 1.8 | 4.0 |
| Methyl Paraben | 0.2 | 0.5 |
| Water | 54.0 | — |

EXAMPLE 12

A composition containing the ingredients listed in Table 12 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 12

| Ingredient | Amount (% wt based on total formulation) | Amount (% wt dry basis) |
| --- | --- | --- |
| Poly (N-vinyl formamide) | 41.2 | 89.5 |
| Glycerin | 2.8 | 6.0 |
| Poly(methyl methacrylate), | 1.8 | 4.0 |

TABLE 12-continued

| Ingredient | Amount (% wt based on total formulation) | Amount (% wt dry basis) |
|---|---|---|
| [Aldrich Chemical Co., Milwaukee, WI] Methyl Paraben | 0.2 | 0.5 |
| Water | 54.0 | — |

EXAMPLE 13

A composition containing the ingredients listed in Table 13 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 13

| Ingredient | Amount (% wt based on total formulation) | Amount (% wt dry basis) |
|---|---|---|
| Poly (N-vinyl formamide) | 41.2 | 89.5 |
| Glycerin | 2.8 | 6.0 |
| Poly (vinyl chloride), [Occidental Chemical Corp., Pottstown, PA] | 1.8 | 4.0 |
| Methyl Paraben | 0.2 | 0.5 |
| Water | 54.0 | — |

EXAMPLE 14

A composition containing the ingredients listed in Table 14 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 14

| Ingredient | Amount (% wt based on total formulation) | Amount (% wt dry basis) |
|---|---|---|
| Poly (N-vinyl formamide) | 41.2 | 89.5 |
| Glycerin | 2.8 | 6.0 |
| Ethyl Cellulose, [Dow Chemical Co., Midland, MI] | 1.8 | 4.0 |
| Methyl Paraben | 0.2 | 0.5 |
| Water | 54.0 | — |

EXAMPLE 15

A composition containing the ingredients listed in Table 15 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 15

| Ingredient | Amount (% wt based on total formulation) | Amount (% wt dry basis) |
|---|---|---|
| Poly (N-vinyl formamide) | 41.2 | 89.5 |
| Propylene Glycol [Sigma Chemical Co., St Louis, MO] | 2.8 | 6.0 |
| Titanium Dioxide | 1.8 | 4.0 |
| Methyl Paraben | 0.2 | 0.5 |
| Water | 54.0 | — |

EXAMPLE 16

A composition containing the ingredients listed in Table 16 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 16

| Ingredient | Amount (% wt based on total formulation) | Amount (% wt dry basis) |
|---|---|---|
| Poly (N-vinyl formamide) | 41.2 | 89.5 |
| Hexylene Glycol [Sigma Chemical Co., St. Louis, MO] | 2.8 | 6.0 |
| Titanium Dioxide | 1.8 | 4.0 |
| Methyl Paraben | 0.2 | 0.5 |
| Water | 54.0 | — |

EXAMPLE 17

A composition containing the ingredients listed in Table 17 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 17

| Ingredient | Amount (% wt based on total formulation) | Amount (% wt dry basis) |
| --- | --- | --- |
| Poly (N-vinyl formamide) | 41.2 | 89.5 |
| Dipropylene Glycol [Union Carbide Corp., Danbury, CT] | 2.8 | 6.0 |
| Titanium Dioxide | 1.8 | 4.0 |
| Methyl Paraben | 0.2 | 0.5 |
| Water | 54.0 | — |

EXAMPLE 18

A composition containing the ingredients listed in Table 18 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 18

| Ingredient | Amount (% wt based on total formulation) | Amount (% wt dry basis) |
| --- | --- | --- |
| Poly (N-vinyl formamide) | 41.2 | 89.5 |
| Propylene Glycol Dicaprylate [Henkel Corp., Ambler PA] | 2.8 | 6.0 |
| Titanium Dioxide | 1.8 | 4.0 |
| Methyl Paraben | 0.2 | 0.5 |
| Water | 54.0 | — |

EXAMPLE 19

A composition containing the ingredients listed in Table 19 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 19

| Ingredient | Amount (% wt based on total formulation) | Amount (% wt dry basis) |
| --- | --- | --- |
| Poly (N-vinyl formamide) | 41.2 | 89.5 |
| Diethylene Glycol [Aldrich Chemical Co., Milwaukee, WI] | 2.8 | 6.0 |
| Titanium Dioxide | 1.8 | 4.0 |
| Methyl Paraben | 0.2 | 0.5 |
| Water | 54.0 | — |

EXAMPLE 20

A composition containing the ingredients listed in Table 20 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 20

| Ingredient | Amount (% wt based on total formulation) | Amount (% wt dry basis) |
| --- | --- | --- |
| Poly (N-vinyl formamide) | 41.2 | 89.5 |
| Sorbitan Monooleate [ICI Americas Inc., Wilmington DE] | 2.8 | 6.0 |
| Titanium Dioxide | 1.8 | 4.0 |
| Methyl Paraben | 0.2 | 0.5 |
| Water | 54.0 | — |

EXAMPLE 21

A composition containing the ingredients listed in Table 21 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch. The procedure removes a substantial fraction of the keratotic plugs initially present in the pores of the skin.

TABLE 21

| Ingredient | Amount (% wt based on total formulation) | Amount (% wt dry basis) |
| --- | --- | --- |
| Poly (N-vinyl formamide) | 41.2 | 89.5 |
| PEG 300 [Sigma Chemical Co., St Louis, MO] | 2.8 | 6.0 |
| Titanium Dioxide | 1.8 | 4.0 |
| Methyl Paraben | 0.2 | 0.5 |
| Water | 54.0 | — |

EXAMPLE 22

A composition containing the ingredients listed in Table 22 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch.

TABLE 22

| Ingredient | Amount (% wt based on total formulation) | Amount (% wt dry basis) |
| --- | --- | --- |
| Poly (N-vinyl formamide) | 27.5 | 59.7 |
| Poly (N-vinyl pyrrolidone) [GAF Corp., New York, NY] | 13.7 | 29.8 |

TABLE 22-continued

| Ingredient | Amount (% wt based on total formulation) | Amount (% wt dry basis) |
| --- | --- | --- |
| Glycerin | 2.8 | 6.0 |
| Titanium Dioxide | 1.8 | 4.0 |
| Methyl Paraben | 0.2 | 0.5 |
| Water | 54.0 | — |

EXAMPLE 23

A composition containing the ingredients listed in Table 23 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch.

TABLE 23

| Ingredient | Amount (% wt based on total formulation) | Amount (% wt dry basis) |
| --- | --- | --- |
| Poly (N-vinyl formamide) | 27.5 | 59.7 |
| Poly (N-vinyl pyrrolidone co-Vinyl Acetate) [BASF Corp., Mount Olive, NJ] | 13.7 | 29.8 |
| Glycerin | 2.8 | 6.0 |
| Titanium Dioxide | 1.8 | 4.0 |
| Methyl Paraben | 0.2 | 0.5 |
| Water | 54.0 | — |

EXAMPLE 24

A composition containing the ingredients listed in Table 24 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch.

TABLE 24

| Ingredient | Amount (% wt based on total formulation) | Amount (% wt dry basis) |
| --- | --- | --- |
| Poly (N-vinyl formamide) | 27.5 | 59.7 |
| Poly (ethylene oxide) [Union Carbide Corp., Danbury, CT] | 13.7 | 29.8 |
| Glycerin | 2.8 | 6.0 |
| Titanium Dioxide | 1.8 | 4.0 |
| Methyl Paraben | 0.2 | 0.5 |
| Water | 54.0 | — |

EXAMPLE 25

A composition containing the ingredients listed in Table 25 is prepared and coated in a manner similar to Example 1. The coated patch is tested on the wetted bridge of the nose in a similar manner as in Example 1. The removed patch displays keratotic plugs, dirt, and other material from the pores of the skin adhered to the surface of the patch. The materials removed from the pores of the skin are clearly visible on the patch.

TABLE 25

| Ingredient | Amount (% wt based on total formulation) | Amount (% wt dry basis) |
| --- | --- | --- |
| Poly (N-vinyl formamide) | 27.5 | 59.7 |
| Dimethicone Copolyol [Wacker Silicones Corp., Adrian, MI] | 13.7 | 29.8 |
| Glycerin | 2.8 | 6.0 |
| Titanium Dioxide | 1.8 | 4.0 |
| Methyl Paraben | 0.2 | 0.5 |
| Water | 54.0 | — |

Examples such as 1–25 can be repeated using copolymers of N-vinyl formamide in place of the polymers of these examples. Such copolymers can be, for example N-vinyl formamide/hydroxyethyl methacrylate (90:10) copolymer or other copolmers of N-vinyl formamide with one or more vinyl copolymers as described in U.S. Pat. No. 5,478,553 the whole of which is incorporated herein by reference. Such copolymers when used in the formulations as noted in the Examples can give advantageous cosmetic products in accordance with this invention.

Those skilled in the art would readily appreciate that all parameters listed herein are meant to be exemplary and that actual parameters will depend upon the desired properties and application for which the compositions, methods and articles of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A cosmetic product for the treatment of skin comprising:

a water-activatable, film-forming polymeric composition formulated to have predetermined properties for allowing desired adhesion of a layer of said composition to the skin of an individual, attachment to keratotic plugs that may be present in the skin, and removal of said keratotic plugs without damage to said skin upon removal of said layer, and a backing material having a first and a second side, said layer being coated on said first side forming a patch, said polymeric composition being selected from the group consisting of copolymers of N-vinyl formamide with at least one vinyl monomer and poly (N-vinyl formamide) homopolymer, with N-vinyl formamide of said polymer composition as a major, active component.

2. The cosmetic product of claim 1 wherein said composition is poly(N-vinyl formamide) comprising 50–100% wt of said composition on a dry basis.

3. The cosmetic product of claim 1 further comprising at least one softening agent.

4. The cosmetic product of claim 1 wherein said composition is formulated to remove more than 10% of keratotic plugs present on an area of skin by peeling a substantially dry layer of said composition from said area of skin.

5. The cosmetic product of claim 1 wherein said composition is formulated to remove more than 20% of keratotic plugs present on an area of skin by peeling a substantially dry layer of said composition from said area of skin.

6. The cosmetic product of claim 1 wherein said composition is formulated to remove more than 35% of keratotic plugs present on an area of skin by peeling a substantially dry layer of said composition from said area of skin.

7. The cosmetic product of claim 1 wherein said backing material comprises at least one layer of said patch, said backing material being formed from a porous, non-woven hydrophobic polymer sheet.

8. A cosmetic product for the treatment of skin comprising:
a non-ionic, non-salt forming polymer composition comprising 50% to 100% of said cosmetic product on a dry basis, said composition being formed as a layer having a first and second side, and further comprising
a backing material attached to said first side of said layer forming a patch,
said product formulated to remove more than 10% of keratotic plugs present on an area of skin by peeling a substantially dry layer of said product from said area of skin.

9. The cosmetic product of claim 8 wherein said composition is formulated to remove more than 20% of keratotic plugs present on an area of skin by peeling a substantially dry layer of said composition from said area of skin.

10. The cosmetic product of claim 8 wherein said composition is formulated to remove more than 35% of keratotic plugs present on an area of skin by peeling a substantially dry layer of said composition from said area of skin.

11. The cosmetic product of claim 8 wherein said non-ionic, non-salt-forming polymer comprises poly(N-vinyl formamide).

12. The cosmetic product of claim 11 further comprising at least one softening agent.

13. The cosmetic product of claim 12 wherein the softening agent is selected from the group comprising: glycerin; propylene glycol; hexylene glycol; dipropylene glycol; propylene glycol dicaprylate; diethylene glycol; sorbitan monopeate; and polyethylene glycol (PEG).

14. The cosmetic product of claim 13 wherein the softening agent is glycerin.

15. The cosmetic product of claim 12 wherein the softening agent comprises 0–20% wt of said composition on a dry basis.

16. The cosmetic product of claim 11 further comprising at least one opacifier.

17. The cosmetic product of claim 16 wherein the opacifier is selected from the group comprising: titanium dioxide; aluminum oxide; silicon dioxide; cellulose acetate butyrate; poly(methyl methacrylate); poly (vinyl chloride); and ethyl cellulose.

18. The cosmetic product of claim 17 wherein the opacifier is titanium dioxide.

19. The cosmetic product of claim 16 wherein the opacifier comprises 0–10% wt of said composition on a dry basis.

20. The cosmetic product of claim 11 further comprising at least one diluent polymer.

21. The cosmetic product of claim 11 wherein the diluent polymer comprises 0–30% wt of said composition on a dry basis.

22. The cosmetic product of claim 11 further comprising at least one preservative.

23. The cosmetic product of claim 11 wherein the preservative is methyl paraben.

24. The cosmetic product of claim 11 wherein the preservative comprises 0–2% wt of said composition on a dry basis.

25. The cosmetic product of claim 11 further comprising at least one solvent.

26. An article for application to skin comprising:
a backing material; and
a composition being selected from the group consisting of copolymers of N-vinyl formamide with at least one vinyl monomer and poly(N-vinyl formamide) homopolymer, said composition forming a layer on one side of said backing material thus forming a patch.

27. The article of claim 26 further comprising a release liner attached to a side of said layer not in contact with said backing material.

28. The article of claim 27 wherein the release liner is formed of polyester.

29. The article of claim 28 wherein the release liner is silicone-coated.

30. The article of claim 26 wherein said composition is poly(N-vinyl formamide) comprising 50–100% wt of said composition on a dry basis.

31. The article of claim 26 wherein said composition further comprises at least one softening agent.

32. The article of claim 26 wherein said composition further comprises at least one opacifier.

33. The article of claim 26 wherein said composition further comprises at least one diluent polymer.

34. The article of claim 26 wherein said composition further comprises at least one preservative.

35. The artical of claim 26 wherein more than 10% of keratotic plugs present on an area of skin can be removed by peeling of said patch with said layer from said area of skin.

36. The article of claim 26 wherein more than 20% of keratotic plugs present on an area of skin can be removed by peeling of said patch with said layer from said area of skin.

37. The article of claim 26 wherein more than 35% of keratotic plugs present on an area of skin can be removed by peeling of said patch with said layer from said area of skin.

38. The article of claim 26 wherein the backing material is formed of a porous, non-woven hydrophobic polymer sheet.

39. The article of claim 26 wherein the backing material is formed of a porous, non-woven hydrophobic polyester sheet.

40. An article for application to skin comprising:
a backing material; and
a composition comprising a non-ionic, non-salt-forming polymer, said composition being coated onto one side of said backing material forming a patch, so that said patch is able to remove more than 10% of keratotic plugs present on an area of skin by peeling of said patch from said area of skin.

41. The article of claim 40 wherein said patch is able to remove more than 20% of keratotic plugs present on an area of skin by peeling of said patch from said area of skin.

42. The article of claim 40 wherein said patch is able to remove more than 35% of keratotic plugs present on an area of skin by peeling of said patch from said area of skin.

43. The article of claim 40 wherein the backing material is formed of a porous, non-woven hydrophobic polymer sheet.

44. The article of claim 40 wherein the backing material is formed of a porous, non-woven hydrophobic polyester sheet.

45. A method for removing keratotic plugs from skin comprising:
providing a composition being selected from the group consisting of copolymers of N-vinyl formamide with at least one vinyl monomer and poly(N-vinyl formamide) homopolymer overlying and in contact with skin having keratotic plugs therein;

allowing said composition to substantially dry; and peeling said composition away from said skin.

46. The method of claim 45 wherein said peeling removes more than 10% of said keratotic plugs present on an area of skin.

47. The method of claim 45 wherein said peeling removes more than 20% of said keratotic plugs present on an area of skin.

48. The method of claim 45 wherein said peeling removes more than 35% of said keratotic plugs present on an area of skin.

49. The method of claim 45 wherein said composition is coated onto a porous backing material before application onto skin.

50. The method of claim 45 wherein said skin is moistened before application of said composition thereto.

51. A method for removing keratotic plugs from skin comprising:

providing a patch that is coated on at least one side with a composition comprising N-vinyl formamide;

applying said composition carried by said patch overlying and in contact with said skin; and removing said patch from said skin.

52. The method of claim 51 comprising the steps of:

moistening said skin;

applying said composition carried by said patch overlying and in contact with the moistened skin;

allowing said composition carried by said patch to substantially dry; and peeling said patch away from said skin.

53. The method of claim 51 comprising the steps of:

moistening said composition carried by said patch;

applying said composition carried by said patch onto said skin;

allowing said composition carried by said patch to substantially dry; and peeling said patch away from said skin.

54. A method for removing more than 10% of keratotic plugs from an area of skin comprising:

providing a patch that is coated on at least one side with a composition comprising a non-ionic, non-salt-forming polymer;

applying said composition carried by said patch overlying and in contact with said skin; and removing said patch from said skin.

55. A method of adhering a patch to skin comprising:

providing a patch that is coated on at least one side with a composition comprising poly(N-vinyl formamide);

applying said patch to moistened skin; and allowing the patch to substantially dry.

56. A method of adhering a patch to skin comprising:

providing a patch that is coated on at least one side with a composition comprising poly(N-vinyl formamide);

moistening the at least one surface of said patch;

applying said moistened patch to said skin; and allowing the patch to substantially dry.

57. A process for manufacturing a patch coated on at least one surface with a composition comprising a solvent-dispersable polymer comprising:

supplying a release liner;

coating said liner with said composition dispersed in a solvent;

partially removing said solvent from said composition by drying;

applying a porous backing material to the partially dried composition;

allowing said composition to partially penetrate into said backing material; and, in a separate step, subjecting the resulting article to subsequent drying to remove additional solvent.

58. The process of claim 57 wherein said partially dried composition is allowed to penetrate into said porous backing material a distance about 30–70% of the cross-sectional thickness of the porous backing material.

59. The process of claim 57 wherein said partially dried composition is allowed to penetrate into said porous backing material a distance about 50% of the cross-sectional thickness of the porous backing material.

60. The process of claim 57 wherein said liner is coated with about 1 to 6 ounces of composition, on a dry weight basis, per square yard of liner.

61. The process of claim 57 wherein said composition is selected from the group consisting of copolymers of N-vinyl formamide with at least one vinyl monomer and poly(N-vinyl formamide) homopolymer.

* * * * *